US007060875B2

(12) United States Patent
Lim et al.

(10) Patent No.: US 7,060,875 B2
(45) Date of Patent: Jun. 13, 2006

(54) METHODS FOR DELAYING LEAF SENESCENCE USING THE ORE7 GENE

(75) Inventors: Pyung-Ok Lim, Pohang-si (KR); Hong-Gil Nam, Pohang-si (KR); Sung-Whan Cho, Pohang-si (KR)

(73) Assignees: Postech Foundation (KR); Genomine, Inc. (KR)

( * ) Notice: Subject to any disclaimer, the term of this patent is extended or adjusted under 35 U.S.C. 154(b) by 0 days.

(21) Appl. No.: 10/487,225

(22) PCT Filed: Aug. 22, 2002

(86) PCT No.: PCT/KR02/01578

§ 371 (c)(1),
(2), (4) Date: Feb. 20, 2004

(87) PCT Pub. No.: WO03/018627

PCT Pub. Date: Mar. 6, 2003

(65) Prior Publication Data

US 2005/0055745 A1    Mar. 10, 2005

(30) Foreign Application Priority Data

Aug. 22, 2001 (KR) ............................... 2001-50774

(51) Int. Cl.
*C12N 15/29* (2006.01)
*C12N 15/82* (2006.01)
*C12N 15/74* (2006.01)
*A01H 4/00* (2006.01)
*C07H 21/00* (2006.01)

(52) U.S. Cl. ..................... 800/290; 800/278; 435/471
(58) Field of Classification Search ............... 536/23.6; 800/278, 290; 435/69.1, 471, 468
See application file for complete search history.

(56) References Cited

U.S. PATENT DOCUMENTS

2003/0061637 A1* 3/2003 Jiang et al. ................. 800/287
2003/0121070 A1* 6/2003 Adam et al. ................. 800/278
2003/0229915 A1* 12/2003 Keddie et al. ............... 800/278
2004/0128712 A1* 7/2004 Jiang et al. ................. 800/278

OTHER PUBLICATIONS

Lewin (1987) Genes III, Wiley & Sons, p. 726.*
Woo Hye Ryun et al., "ORE9, an F-Box Protein That Regulates Leaf Senescence in Arabidopsis," *Plant Cell*, 2001, pp. 1779-1790, 13(8), Ameri. Soc. of Plant Physiologists, Rockville, MD.
Gan, Susheng et al., "Making Sense of Senescence," *Plant Physiol.*, 1997, pp. 313-319, 113(2), Amer. Soc. of Plant Physiologists Lancaster, PA.
Buchanan-Wollaston, V., "The molecular biology of leaf senescence," *J. Exp. Bot.*, 1997, pp. 181-199, 48(307), Rockefeller Univ. Press, New York.
John, Isaac et al., "Cloning and characterization of tomato leaf senescence-related cDNAs," *Plant Mol. Biol.*, 1997, pp. 641-651, 33(4), Kluwer Academic, Dordrecht, Holland.
Nam, HongGil, "The molecular genetic analysis of leaf senescence," *Curr. Opin. Biotechnol.*, 1997, pp. 200-207, 8(2), Current Biology, London, England.
Oh, Sung Aeong et al., "Identification of three genetic loci controlling leaf senescence in *Arabidopsis thaliana*," *Plant Jnl.*, 1997, pp. 527-535, 12(3), Blackwell Sciences, Oxford, England.
Oh, S.A. et al., "A senescence—associated gene of *Arabidopsis thaliana* is distinctively regulated during natural and artificially induced leaf senescence," *Plant Mol. Biol.*, 1996, pp. 739-754, 30(4), Kluwer Academic, Dordrecht, Holland.
Thomas, H. et al., "Gene expression in leaves of *Arabidopsis thaliana* induced to senesce by nutrient deprivation," *J. Exp. Bot.*, 1996, pp. 1845-1852, 47(305), Rockefeller Univ. Press, New York.
Yao, et al., "Gene Expression and Regulation in Leaf Senescence", Hereditas (Beijing), 1999, pp. 63-65, 21(4).
Weaver et al., "Leaf Senescenence: Gene Expression and Regulation and Regulation", *Genetic Engineering*, 1997, pp. 215-234, vol. 19, Pelenum Press, New York.
Hajouj et al., "Identification of regulatory and metabolic genes associated with leaf senescence", Curr. Plant Sci. Biotechnol. Agric., 1999, pp. 487-490, Kluwer Academic Publishers, Dordrecht, Holland.
NCBI Acession #AF, 194974, "Activation Tagging in Arabidopsis", 1999.
Shen et al., *Zhiwu Shenglixue Tongxun*, pp. 304-312, vol. 24, No. 4.

* cited by examiner

*Primary Examiner*—Ashwin D. Mehta
*Assistant Examiner*—Cathy K. Worley
(74) *Attorney, Agent, or Firm*—Buchanan Ingersoll PC

(57) ABSTRACT

The present invention relates to a gene regulating leaf longevity of plants and a method for regulating the longevity of plants using the same. More particularly, it relates to a ORE7 gene regulating leaf longevity of plants which has a nucleotide sequence represented by SEQ ID NO: 1, and to a method for regulating the longevity of plants, in which the ORE7 gene is introduced into the plants and overexpressed, thereby delaying senescence of the plants. Plants can be transformed with ORE7 gene according to the present invention, so that the longevity of the plants is extended, thereby improving productivity and storage efficiency of the plants. Furthermore, the ORE7 gene and an ORE7 protein expressed therefrom according to the present invention are useful for studies of senescence mechanisms, and for identification of senescence-associated genes or senescence inhibitory substances, in plants.

9 Claims, 14 Drawing Sheets

METHODS FOR DELAYING LEAF SENESCENCE USING THE ORE7 GENE

TECHNICAL FIELD

The present invention relates in general to a gene regulating leaf longevity of plants and a method for regulating the longevity of plants using the same. More particularly, it relates to a gene ORE7 regulating leaf longevity of plants which has a nucleotide sequence represented by SEQ ID NO: 1, and to a method for regulating the longevity of plants, in which the gene ORE7 is introduced into the plants and overexpressed, thereby delaying senescence of the plants.

BACKGROUND ART

Senescence is the final stage that plants undergo during their lifetime. The initiation of senescence can be said to be a rapid changeover point in a plant's development stage. As senescence progresses, a plant's synthesis ability gradually decreases and it loses cellular homeostasis with successive degradation of intracellular structures and macromolecules, finally leading to death (Matile P. et al., *Elservier*, 413–440, 1992; Nooden L. D. et al., *Academic press*, 1988; Thiman K. V. et al., *CRC press*, 85–115, 1980; and Thomas H. et al., *Annu. Rev. Plant Physiol.*, 123:193–219, 1993). Such senescence of plants is a series of continuous biochemical and physiological phenomena, which is genetically destined to progress in highly intricate and active manners at cell, tissue and organ levels. However, the senescence of plants is seen as a process of cellular degeneration, and at the same time, a genetic character which is actively acquired for adaptation to environment during the development process, including migration of nutrients from growth organs to genital organs at the winter season.

The suppression of plant senescence is not only of great scientific importance in itself, but also of great industrial importance in terms of the productivity of crops or the possibility of improving post-harvest storage efficiency. For this reason, genetic, molecular biological, physiological and biochemical studies have been actively conducted in the attempt to establish plant senescence phenomena. However, reports regarding phytohormones are the main area of interest; studies on senescence regulation, such as the induction of senescence regulation using senescence regulatory genes, are, as yet, insufficient.

Cytokinin, a plant growth hormone, is known as a hormone capable of physiologically delaying senescence. For this reason, there have been studies conducted to delay senescence by regulation of cytokinin synthesis, but there were problems in that other physiological actions are also affected due to the influence of hormones. However, there has been recent success in delaying the progression of senescence by a method in which an IPT gene is linked to a promoter of a senescence-specific SAG12 gene so that the synthesis of cytokinin is specifically regulated at a certain senescence stage. In the case of tobacco plants whose senescence was delayed by this method, an increase of more than 50% in productivity could be achieved while causing little or no changes in the blooming time and no other deformations (Gan S. et al., *Science*, 22:1986–1988, 1995). Moreover, plants for delay of senescence have been developed, making the ripe tomatoes a main object of this development. For such development, the following methods have been applied; inhibition of synthesis of ethylene, a phytohormone playing an important role in senescence, or reduction of the amount of intracellular ethylene (Klee et al., *Plant Cell*, 3(11): 1187–93, 1991; and Picton et al., *Plant Physiol.*, 103(4): 1471–1472, 1993).

In addition, studies on delay of senescence are mainly focused on the manipulation of degradation-associated genes, which have activities associated with biochemical changes occurring in a process of senescence or are involved in the signal transduction system. A typical example connected with such studies includes commercialized tomatoes, called "Flavr savr", in which the expression of polygalacturonase gene involved in the degradation of cell walls is impeded using antisense DNA so that the softening of tomatoes is prevented, thereby improving the transport and storage properties of tomatoes (Giovannoni et al., *Plant Cell*, 1(1): 53–63, 1989). It was also reported that, where the expression of phospholipase D involved in degradation of lipids is impeded with the antisense DNA, senescence caused by phytohormones is delayed (Fan et al., *Plant Cell*, 9(12): 2183–96, 1997). Furthermore, it was recently reported that leaf senescence is delayed, in tobacco plants in which SAG12 promoter, and kn1 (knotted 1), a homeobox gene of corn, are expressed (Ori et al., *Plant Cell*, 11:917–927, 1999).

However, a method capable of more directly regulating senescence involves isolating mutant of senescence-associated genes and analyzing genes which cause the mutation. According to existing reports, it is known that, in *Arabidopsis thaliana*, the expression of ethylene receptors is controlled in a ripening period of fruits or in the senescence process of flowers (Payton S. et al., *Plant Mol. Biol.*, 31(6): 1227–1231, 1996), and the expression of clp gene is regulated in a senescence process of leaves. Recently reported were studies on the identification of genes involved in a senescence process of leaves (Oh S. A. et al., *Plant Mol. Biol.*, 30(4): 739–754, 1996), and on the isolation of leaf senescence-delaying mutants from *Arabidopsis thaliana* (Oh S. A. et al., *The Plant Journal*, 12(3):527–535, 1997). Also, a mutant gene was successfully isolated from an ore9 mutant of the leaf senescence-delaying mutants (Woo H. R. et al., *Plant Cell*, 13: 1779–1790, 2001). In addition, activities of a promoter of sen1, a senescence-associated gene, were reported (Oh S. A., et al., *Journal of Plant Physiology* 151:339–345, 1997). However, studies on genes that directly regulate senescence and their functions are, as yet, insufficient.

DISCLOSURE OF THE INVENTION

Therefore, the object of the present invention is to provide a gene regulating leaf longevity of plants.

Another object of the present invention is to provide a method for regulating leaf longevity of plants using the gene.

To accomplish the object of the present invention, the present invention provides a gene ORE7 regulating the leaf longevity of plants, which has a nucleotide sequence represented by SEQ ID NO: 1.

In addition, to accomplish another object of the present invention, the present invention provides a method for regulating the longevity of plants, in which the gene ORE7 is introduced into the plants and overexpressed, thereby delaying senescence of the plants.

As used herein, the term 'longevity-extended mutant ore7' or 'ore7 mutant' means a mutant whose ORE7 gene is activated by an activation tagging method so that the mutant exhibits a senescence-delaying phenotype.

Hereinafter, the present invention will be described in detail.

In the present invention, in order to investigate genes involved in regulation of longevity in plants, mutants exhibiting the longevity-extended character were selected. For this, *Arabidopsis thaliana*, frequently used as the subject for genetic and molecular studies of plants, was used as a test plant.

Mutation induction methods which have generally been used to identify functions of genes are specifically divided into the following three methods: (1) A chemical method of inducing mutations by treatment with chemicals, such as ethyl-methyl sulfonic acid (EMS), (2) A method of inducing mutation by X- or γ-ray irradiation, and (3) A method of inducing mutation by transformation with T-DNA of *Agrobacterium*, a soil bacterium. The method of inducing the mutation by the chemical treatment, the X- or γ-ray irradiation or the T-DNA insertion as described above, destroys a part or the whole of an original gene so that intrinsic functions of the gene are lost. Therefore, the functions of the genes can be deducted through the above methods. However, mutations formed by these methods are mostly recessive mutations, and if other genes with functions similar to the destroyed gene are present in a genome, the phenotype is not exhibited due to the other similar genes. Furthermore, if the destroyed gene is a key, it is disadvantageous in that lethality of plants may be caused.

On the contrary, the activation tagging method used in the present invention is advantageous in that it can induce the phenotype even when genes with duplicate functions are present at other sites in genome of *Arabidopsis thaliana*, because T-DNA artificially activates the expression of genes in plants without destroying a nucleotide sequence of the genes (Weigel et al., *Plant Physiology*, 122:1003–1014, 2000). More specifically, the activation tagging method utilizes an activation tagging vector which has a selection marker, a replication origin required for replication in *E. coli*, and an ampicillin-resistant gene, within T-DNA, in order to easily separate the surrounding DNA forming a boundary with T-DNA. Furthermore, the activation tagging vector has four 35S CaMV enhancers in the right border of T-DNA. Therefore, when T-DNA is inserted into a genome of plants, it activates genes around sites inserted with the T-DNA, thereby inducing mutations (see FIG. 6). In this case, even if other genes with similar functions are present in genome, the phenotype can be exhibited by the genes activated by the enhancers. Therefore, when the activation tagging method is applied in order to identify senescence regulatory genes, there is a high possibility for investigation of novel senescence regulatory genes that cannot be investigated by the loss-of-function mutation approach. In addition, the activation tagging method is advantageous in that it induces dominant mutations so that the mutant phenotype is observed one generation in advance. Accordingly, the present inventors have selected mutants with extended leaf longevity in *Arabidopsis thaliana* mutants produced by the activation tagging method, and investigated genes involved in an extended longevity of the selected mutants.

In one embodiment of the present invention, in order to select mutants with extended leaf longevity in *Arabidopsis thaliana*, mutants were produced using an activation tagging vector pSKI015. Then, of the grown individuals, an individual with a slow yellowing rate was selected with the naked eye, and termed 'ore7'. Following this, to verify longevity-extending character of the ore7 mutant, it was examined for changes in photosynthesis activity and chlorophyll content. Results indicated that, in the wild type, the photosynthesis activity and the chlorophyll content were completely lost at 40 days after germination (DAG), but in the longevity-extended mutant ore7, about 100% of the photosynthesis activity and about 78% of the chlorophyll content were maintained at the same period (see FIGS. 1B and 1C).

In another embodiment of the present invention, in order to verify that an extension of longevity in the ore7 mutant is affected not only at a physiological level but also at a molecular level, the expression patterns of various senescence-associated genes were examined by northern blot analysis. Results indicated that, in the wild type, the expression of SEN4 and SAG12 genes, that are already known to increase at a senescence stage, were increased rapidly as senescence progresses, whereas in the ore7 mutant, the expression of these senescence-associated genes were not substantially increased. On the contrary, in the case of the wild type, the expression of chlorophyll a/b binding protein gene which had been increased during anabolic action, such as photosynthesis, was significantly decreased in proportion to the progression of senescence, but in the ore7 mutant of the present invention, there was little or no change in the expression of this gene (see FIG. 1D).

Meanwhile, although leaf senescence is seen to be destined in genes, the progression of senescence can be accelerated by dark treatment (Oh et al., *Plant J.*, 12: 527–535, 1997). Therefore, the present inventors examined a change in leaf longevity of the ore7 mutant according to the dark treatment by measuring changes in photosynthesis activity and chlorophyll content. Examination of the progression of senescence caused by the dark treatment indicated that, in the wild type, the chlorophyll content and the photosynthesis activity were significantly decreased at about 5 days after the dark treatment, but in the ore7 mutant, they were decreased by only 3% and 22%, respectively (see FIGS. 2B and 2C). Furthermore, results of analysis for the expression of SEN4 gene, a measure of senescence molecules, indicated that the expression of SEN4 in the wild type was highly increased compared to the ore7 mutant (see FIG. 2D).

Moreover, leaf senescence is known as being accelerated by phytohormones, such as abscisic acid (ABA), methyl jasmonate (MeJA) and ethylene (Hensel et al., *Plant Cell* 5:553–564, 1993). Therefore, in order to examine a change in leaf longevity in the ore7 mutant under treatment with such phytohormones, the progression of senescence was measured by examining chlorophyll contents and photosynthesis activities after the ore7 mutant had been treated with ABA, MeJA and ethylene, respectively. As a result, it was found that, in the wild type, both the chlorophyll content and the photosynthesis activity were significantly reduced by influencing the phytohormones, resulting in accelerated senescence. However, in the ore7 mutant, the effect of the phytohormones was highly reduced, so that the ore7 mutant can have an extended longevity even if it is treated with the senescence-accelerating hormones (see FIGS. 3 and 4). Furthermore, results of analysis of SEN4 gene, a measure of senescence molecules, indicated that the expression of SEN4 in the wild type is highly increased, compared to the ore7 mutant (see FIG. 5). This suggests that the longevity-extending effect is exhibited at the physiological level and at the molecular level.

In the other embodiment of the present invention, a gene involved in an extension in longevity of plants was isolated from the ore7 mutant by a plasmid rescue method (Weigel et al., *Plant Physiology*, 122:1003–1014, 2000). A nucleotide sequence of a DNA fragment located around a site inserted with T-DNA that had been isolated by this plasmid resque method was then determined.

The determined nucleotide sequence was searched with a genome database of *Arabidopsis thaliana*. As a result, an open reading frame (ORF) located most adjacent to the enhancers was found. It was determined that the isolated gene is the gene which has a single exon and consists of 936 nucleic acids encoding 311 amino acids. This gene was termed 'ORE7'. A nucleotide sequence of the ORE7 gene is represented by SEQ ID NO: 1. A database search for a peptide sequence deduced from the determined sequence of the OER7 gene identified that a protein expressed from the ORE7 gene consists of 311 amino acids, as represented by SEQ ID NO: 2, and contains an AT-hook motif. It is known that the AT-hook motif is bound to an AT-rich region of a promoter of a target gene so that it directly serves as a transcription factor, or as a transcription regulator aiding the transcription factor in getting close to the promoter, or involves in chromosome architecture like histone (Aravind et al., *Nucleic Acids Res.* 26(19): 4413–4421, 1998). Furthermore, it was found that the ORE7 protein has glycine-, histidine-, glutamine-, and glutamic acid-rich motifs which are commonly found in the transcription regulators (Abraham et al., *Gene*, 255:389–400, 2000; and Fujimoto et al., *Biochem. Biophys. Res. Commun.*, 280(1): 164–171, 2001).

In order to verify whether the senescence-delaying phenotype of the ore7 mutant is caused by overexpression of the ORE7 gene, northern blot analysis was carried out using the ORE7 gene as a probe. As a result, in the wild type, the expression of the ORE7 gene was not observed, but in the ore7 mutant, the overexpression of the ORE7 gene was observed (see FIG. 7). Furthermore, the ORE7 gene was re-introduced into the wild type *Arabidopsis thaliana* so as to be overexpressed, and examination was carried out to determine whether the leaf senescence-delaying phenotype is reproduced. At this time, as s vector, a pCAMBIA3301 vector is preferably used, although the known vectors for plant transformation may also be used without limitation. Moreover, as a host to be transformed, although all microorganisms belonging to an *Agrobacterium* sp. May be used without limitation, *Agrobacterium tumefacience* strain was termed 'pAT-ORE7' and deposited under the accession number KCTC 10032BP on Aug. 8, 2001 with the Korean Collection for Type Cultures (KCTC) at the Korean Research Institute of Bioscience and Biotechnology (KRIBB), #52, Oun-dong, Yusong-ku, Taejon 305–333, Republic of Korea.

Then, the wild type *Arabidopsis thaliana* (Columbia) was transformed with the pAT-ORE7 by the floral tip method (Clough et al, *Plant J.*, 16(6): 735–743, 1998). It was found that the longevity-extending phenotype is reproduced in the transformed *Arabidopsis thaliana*. This suggests that the ORE7 gene according to the present invention is the gene which inhibits leaf senescence in *Arabidopsis thaliana*.

Sequencing of a protein expressed from the ORE7 gene of the present invention showed that sequence found in the transcription factors or transcription regulators is present in amino acid sequence of the protein. Accordingly, since the ORE7 protein expressed from the ORE7 gene was deduced to be the transcription factor or transcription regulator that regulates the expression of genes in nuclei, the present inventors confirmed whether the ORE7 protein migrates into the nuclei. For this, a recombinant plasmid which allows the ORE7 gene of the present invention to be expressed in the form of a fusion protein with a green fluorescence protein (GFP) was constructed by a method of Kain et al. (Kain et al. *Biotechniques*, 19(4): 650–655, 1995). Observation with a fluorescence microscope showed that the expression of GFP occurs in the nuclei (see FIG. 8). This suggests that the ORE7 protein migrates into the nuclei and functions therein.

The ORE7 gene of the present invention may function as the transcription repressor for inhibiting the transcription factor which regulates the initiation of leaf senescence, and also as a negative regulator directly inhibiting the initiation and progression of senescence. In addition, the ORE7 gene of the present invention may exhibit a function of increasing hormones, such as cytokinin or auxin, senescence inhibitory hormones, thereby indirectly inhibiting senescence.

Meanwhile, the present invention provides a method for extending the longevity of plants, by transforming the plants with a vector that was constructed in such a manner that the ORE7 gene is overexpressed. As a method for producing the transgenic plants in which the ORE7 gene was overexpressed, plant transformation methods known in the art can be used. For example, an *Agrobacterium*-mediated transformation method using a binary vector for plant transformation introduced with the ORE7 gene can be used. In addition, when a vector not containing a T-DNA region is used, electroporation, microparticle bombardment, polyethylene glycol-mediated uptake and the like may be used.

Plants whose longevity can be extended by the method of the present invention include food crops comprising rice plant, wheat, barley, corn, bean, potato, Indian bean, oat and Indian millet; vegetable crops comprising *Arabidopsis* sp., Chinese cabbage, radish, red pepper, strawberry, tomato, watermelon, cucumber, cabbage, melon, pumpkin, welsh onion, onion and carrot; special crops comprising ginseng, tobacco plant, cotton plant, sesame, sugar cane, sugar beet, *Perilla* sp., peanut and rape; fruit trees comprising apple tree, pear tree, jujube tree, peach tree, kiwi fruit tree, grape tree, citrus fruit tree, persimmon tree, plum tree, apricot tree and banana tree; flower crops comprising rose, gladiolus, gerbera, carnation, chrysanthemum, lily and tulip; and fodder crops including ryegrass, red clover, orchardgrass, alfalfa, tallfescue and perennial ryegrass, etc. Particularly, when the method of the present invention is applied to edible greens or fruits such as tomatoes, which have a thin pericarp and thus show rapid deterioration in quality caused by senescence, and to plants whose leaf is mainly marketed, it effectively increases the storage efficiency of the plants.

Furthermore, the ORE7 gene and ORE7 protein of the present invention are useful for investigation of senescence-associated genes or senescence inhibitory substances in plants. In addition, the gene of the present invention can be used to investigate senescence inhibitory substances by investigating substances binding to the genes of the present invention or substances inhibiting or activating the expression of the ORE7 gene. Specifically, investigation can be performed by various conventional methods including DNA chip, protein chip, polymerase chain reaction (PCR), northern blot analysis, southern blot analysis, western blot analysis, enzyme-linked immunosorbent assay (ELISA) and 2-D gel analysis and the like.

BRIEF DESCRIPTION OF THE DRAWINGS

SAG12: a senescence-associated gene
SEN4: a senescence-associated gene
Cab: a gene of chlorophyll a/b binding protein

0D: before dark treatment
4D: at 4 days after dark treatment

Figure 3:
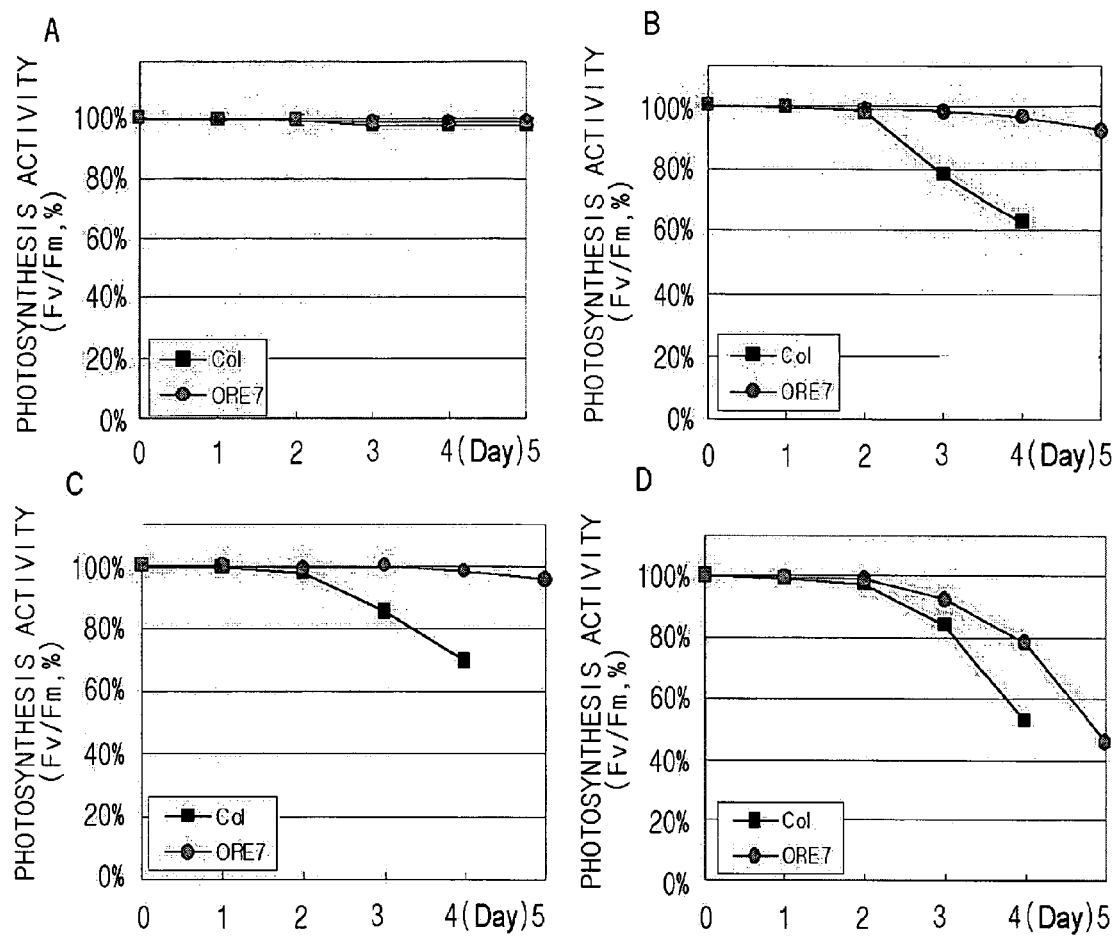

FIG. 3 is a graph showing a change in photosynthesis activity depending on time, after treatment with a MES buffer solution (negative control group) (A), MeJA (B), ABA (C) and ethylene (D), which are senescence-accelerating hormones, in the wild type *Arabidopsis thaliana* (Col) and the longevity-extended mutant ore7.

Figure 4:
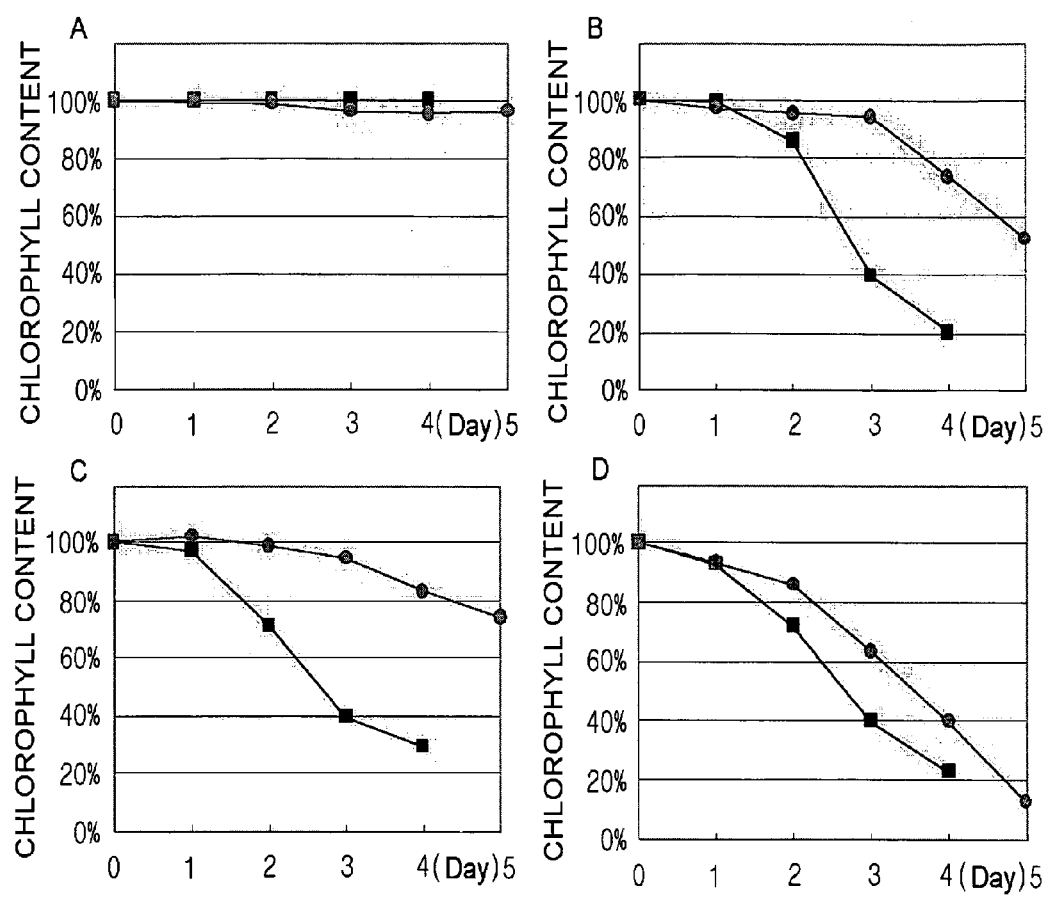

FIG. 4 is a graph showing a change in chlorophyll content depending on time, after treatment with MES buffer solution (negative control group) (A), MeJA (B), ABA (C) and ethylene (D), which are senescence-accelerating phytohormones, in the wild type *Arabidopsis thaliana* (Col) and the longevity-extended mutant ore7.

Figure 5:
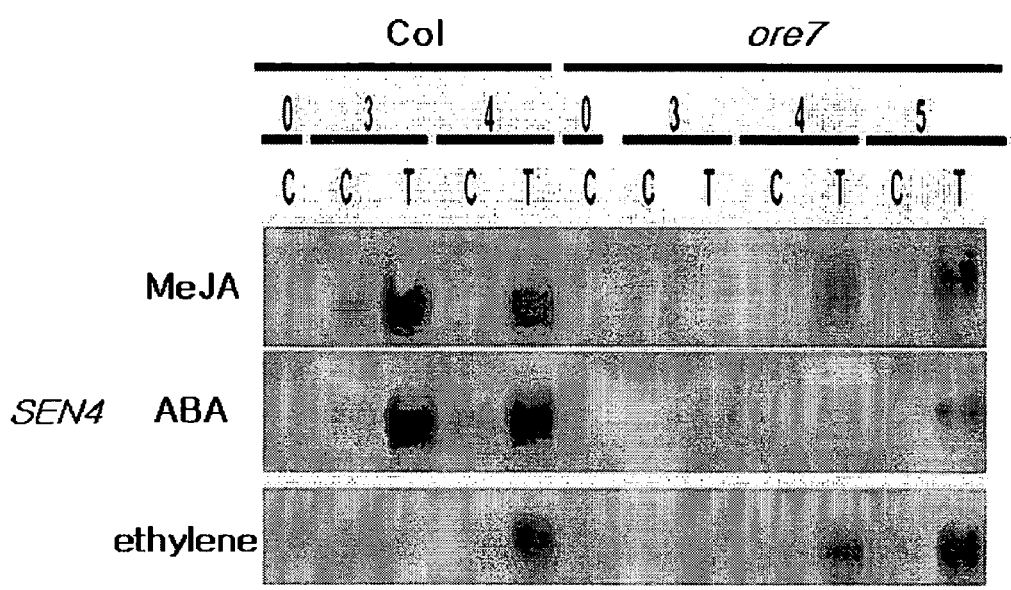

FIG. 5 shows the results of northern blot analysis illustrating the expression pattern of a senescence-associated gene (SEN4) depending on time, at 0, 3, 4 and 5 days after treatment with MeJA, ABA and ethylene, respectively, which are senescence-accelerating hormones, in the wild type *Arabidopsis thaliana* (Col) and the longevity-extended mutant ore7.

C: a control group not treated with the senescence-accelerating hormones
T: a group treated with the senescence-accelerating hormones.

Figure 6:
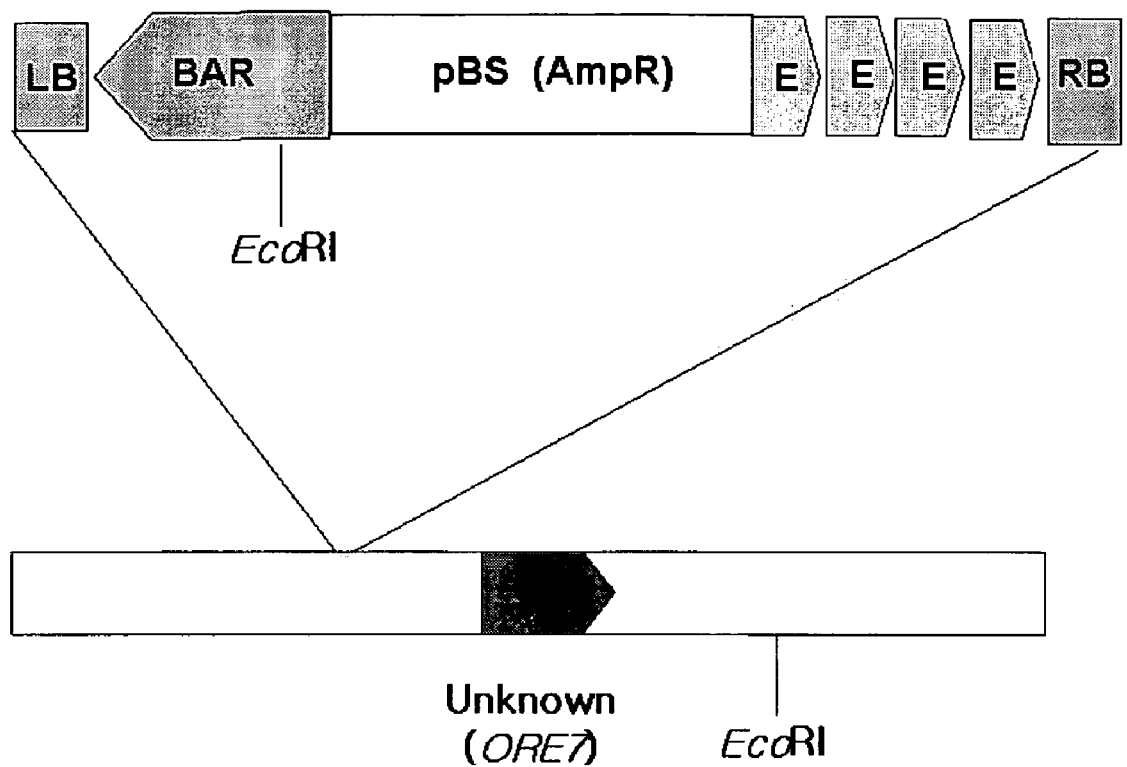

FIG. 6 is a scheme showing that an activation tagging vector pSKI015 is inserted into a genome of the longevity-extended mutant ore7.

Figure 7:
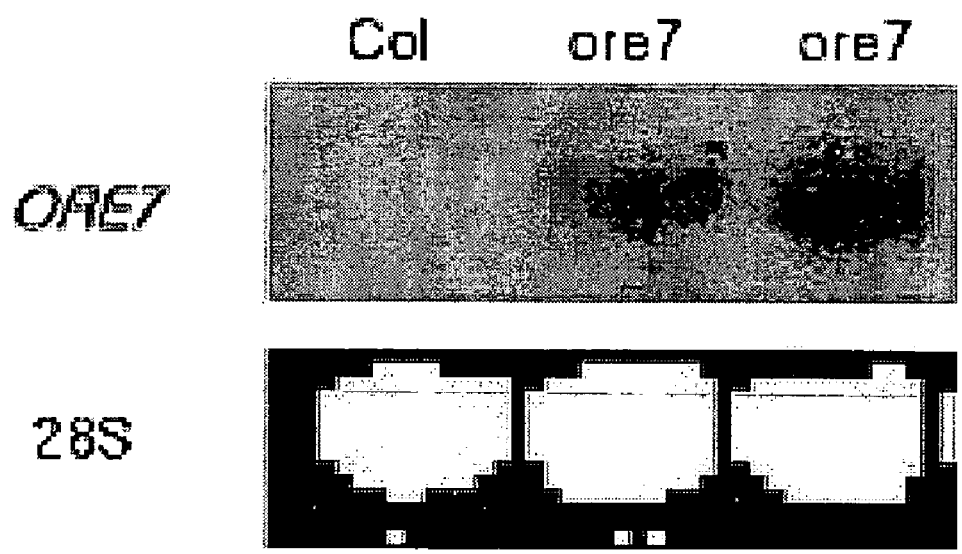

E: an enhancer
BAR: a herbicide-resistant gene
pBS: a region containing a replication origin of *E. coli* and an ampicilin-resistant gene FIG. 7 shows the results of northern blot analysis illustrating the expression of an ORE7 gene in the wild type *Arabidopsis thaliana* (Col) and in the longevity-extended mutant ore7, in which 28S is a control group.

Figure 8:
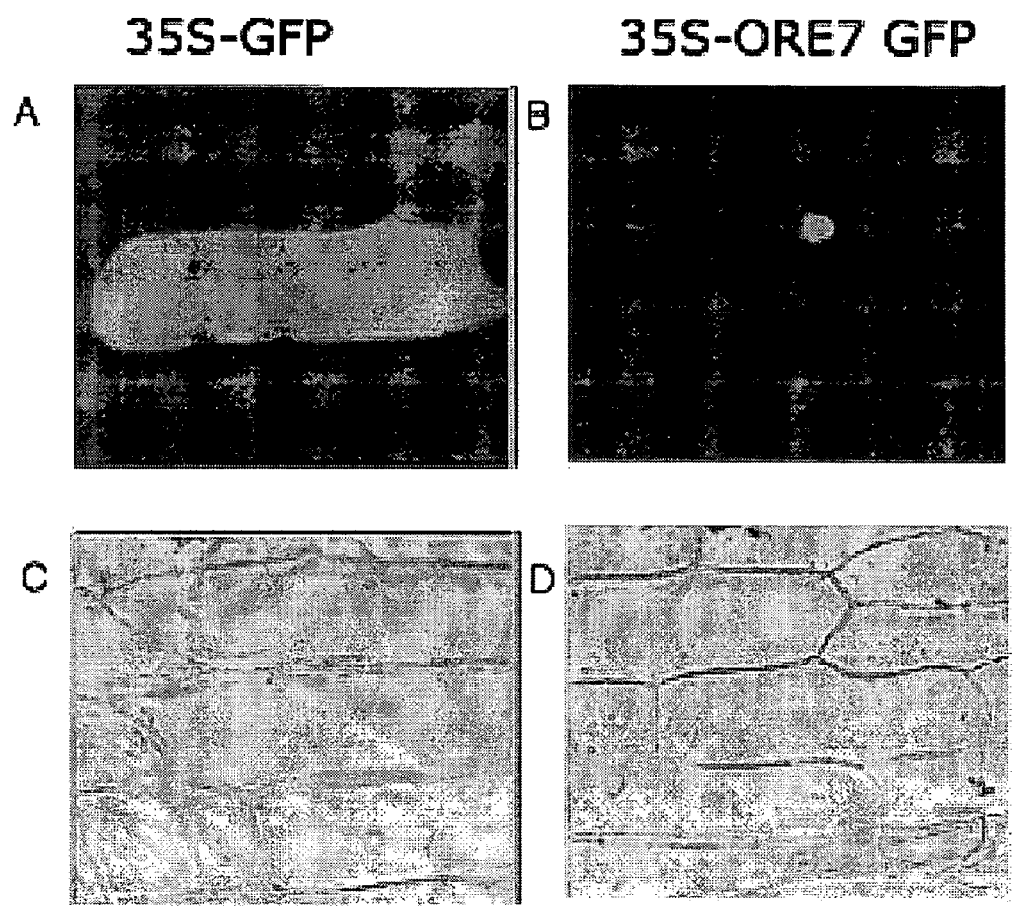

FIG. 8 is a photograph showing migration of a GFP-ORE7 fusion protein into a nucleus, in an epidermal cell of onions, observed under a fluorescence-(A and B) and an optical microscope (C and D).

A: a photograph of 35S-GFP (a positive control group)
B: a photograph of 35S-ORE7-GFP
C: a photograph of 35S-GFP (a positive control group)
D: a photograph of 35S-ORE7-GFP

BEST MODE FOR CARRYING OUT THE INVENTION

The present invention will hereinafter be described in further detail by examples. It should however be borne in mind that the present invention is not limited to or by the examples.

EXAMPLE 1

Selection of Longevity-extended Mutant from *Arabidopsis thaliana*

Figure 1A:
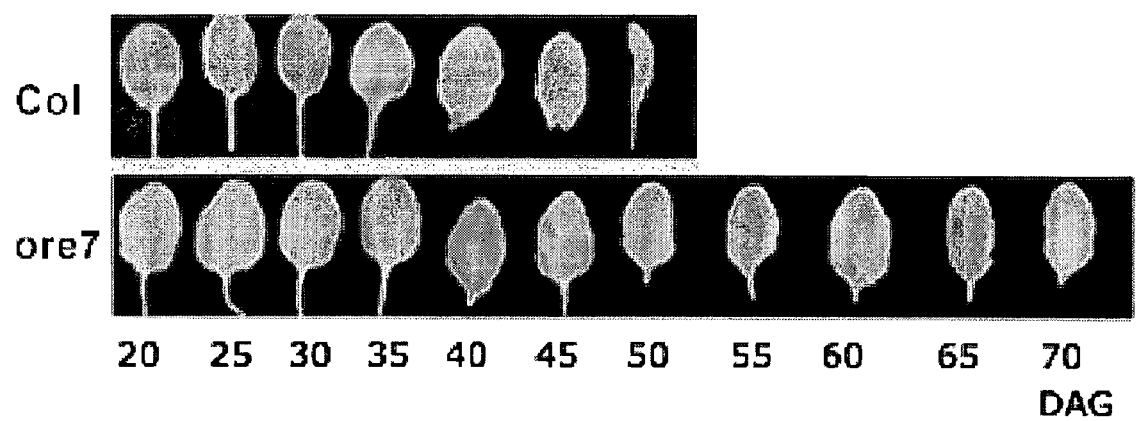
FIG. 1A is a photograph illustrating leaf senescence depending on time, in the wild type *Arabidopsis thaliana* (Col) and in the longevity-extended mutant ore7.

First, in order to induce mutations in *Arabidopsis thaliana*, pSKI015 (Weigel et al., *Plant Physiology*, 122: 1003–1014, 2000; obtained from Weigel's Lab., USA), an activation tagging vector, was introduced into an *Agrobacterium tumefacience* ABI strain (obtained from Amasino's Lab., USA) by the known electroporation method, and then cultured in a medium containing kanamycin and carbenicillin in order to select transformants. Following this, the wild type *Arabidopsis thaliana* (Columbia) was transformed with the *Agrobacterium tumefacience* ABI strain inserted with pSKI015, according to the floral dip method (Clough et al., *Plant J.*, 16(6): 735–743, 1998). The transformed *Arabidopsis thaliana* was bred, thereby obtain seeds, and herbicide-resistant transformants were selected from the seeds. Approximately 5000 T1 lines were then grown in a greenhouse at a controlled temperature of 23° C., and the yellowing of leaves, caused by a reduction in chlorophyll according to age-dependent plant senescence, was observed with the naked eye. One line of mutants which had a slow yellowing rate compared to the wild type was then selected. This selected mutant was termed 'ore7'. FIG. 1A shows the senescence pattern of leaves depending on time, in the wild type *Arabidopsis thaliana* and in the longevity-extended mutant ore7.

EXAMPLE 2

Examination on Expression of Characters in Longevity-extended Mutant ore7

In order to verify a longevity-extending character of the ore7 mutant, a rosette leaf 3 of T2 generation plant was observed with the naked eye, every five days, after 20 DAG, and measured for chlorophyll content, photosynthesis activity. The results were compared with those of the wild type *Arabidopsis thaliana*. Sample groups in this case were 25 independent leaves obtained from each individual.

2-1) Measurement of the Chlorophyll Content

Figure 1B:
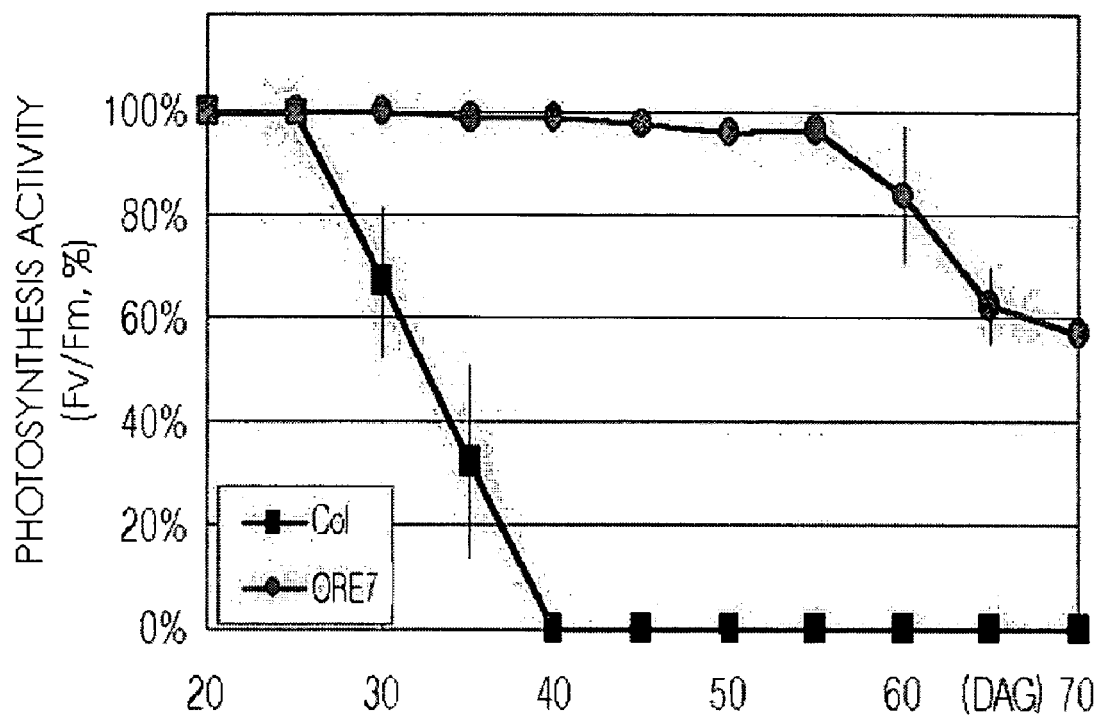
FIG. 1B is a graph showing changes in photosynthesis activity depending on time, in the wild type *Arabidopsis thaliana* (Col) and in the longevity-extended mutant ore7.

In order to measure the chlorophyll content, the respective sample leaves were boiled in 95% ethanol at 80° C., thereby extracting chlorophyll. The chlorophyll content was measured at absorbance of 648 nm and 664 nm, and expressed as chlorophyll concentration per fresh weight of leaves (Vernon et al., *Anal. Chem.*, 32:1142–1150, 1960). As shown in FIG. 1B, results showed that the chlorophyll content of the wild type was rapidly decreased after 25 DAG and become 0% at 40 DAG, whereas ore7 mutant exhibited a chlorophyll content of more than 70% of the initial chlorophyll content even at 40 DAG.

2-2) Measurement of Photosynthesis Activity

Figure 1C:
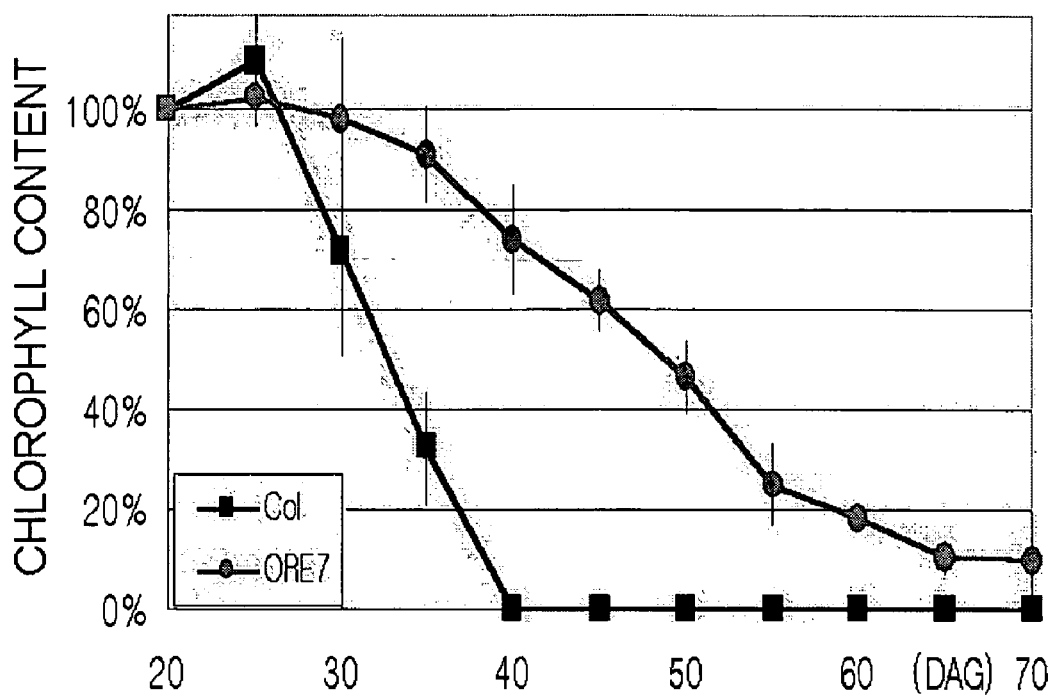
FIG. 1C is a graph showing changes in chlorophyll content depending on time, in the wild type *Arabidopsis thaliana* (Col) and in the longevity-extended mutant ore7.

In order to measure photosynthesis activity, a method of Oh et al. (Oh S. A. et al., *Plant Mol. Biol.,* 30: 939, 1996), was used. First, leaves at the respective DAG were dark-treated for 15 minutes and measured for fluorescence of chlorophylls using Plant Efficiency Analyzer (Hansatech). The photosynthesis activity was expressed as photochemical efficiency of photosystem II (PS II) using a fluorescent property of chlorophylls. The photochemical efficiency was expressed as the ratio of maximum variable fluorescence (Fv) to maximum value of fluorescence (Fm) (Fv/Fm). As the ratio is increased, the photosynthesis activity improves. As shown in FIG. 1C, results indicated that, in the wild type, the photosynthesis activity was started to reduce rapidly after 30 DAGs, and almost lost after 40 DAG, whereas in the ore7 mutant, it was started to reduce after 40 DAG and maintained at about 60% even at 70 DAG due to very slow reduction patterns thereof.

According to the said results, the ore7 mutant has phenotypes of far longer leaf longevity than the wild type. This longevity-extending effect can be verified from the fact that the biochemical changes according to senescence, expressed as a reduction in chlorophyll content and a reduction in photosynthesis activity, occur later than in the wild type.

EXAMPLE 3

Examination of Expression of Senescence-associated Genes in ore7 Mutant

In order to compare the expression of senescence-associated genes (SAGs) in the ore7 mutant with that in the wild type, the expression patterns of the respective SAG genes depending on the passage of time during a process of leaf development were identified by northern blot assay. Total RNA extracted from respective leaves at 22, 26, 30, 34 and 38 DAG using Tri-reagent (Sigma) was used as samples (Woo H. R. et al., *Plant Cell,* 13:1779–1790, 2001). 10 µg of RNA was loaded in every lane, and a SAG12 gene, a SEN4 gene and a Cab gene were used as probes.

Figure 1D:
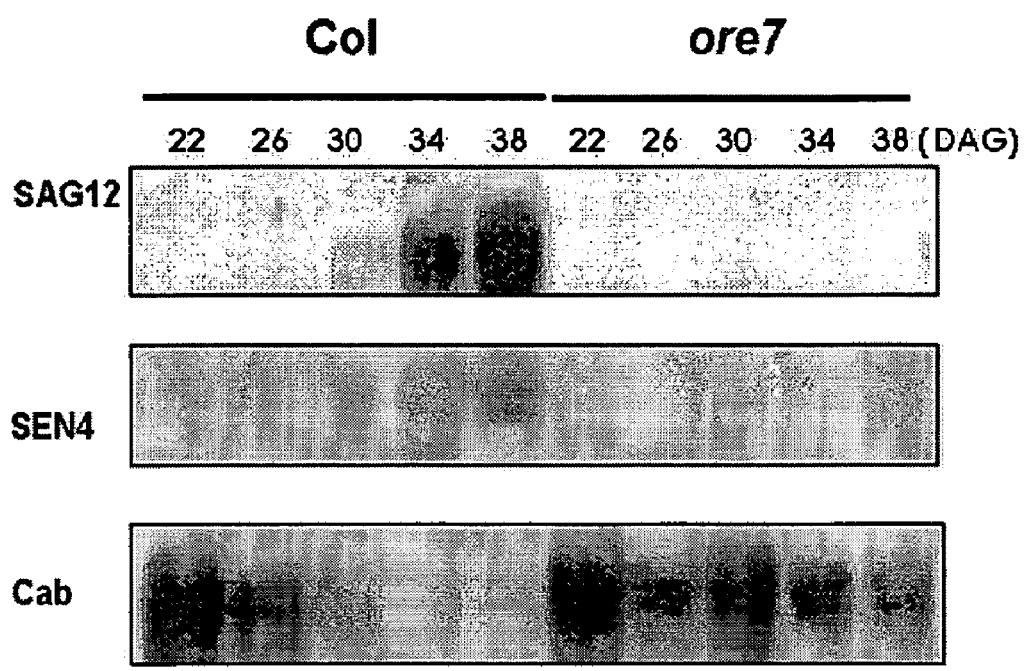
FIG. 1D shows the results of northern blot analysis illustrating the expression patterns of senescence-associated genes and a photosynthesis-associated gene depending on time, in the wild type *Arabidopsis thaliana* (Col) and in the longevity-extended mutant ore7.

Results showed that the expression of a photosynthesis-associated gene, such as chlorophyll a/b binding protein (Cab) was reduced in proportion to senescence with the passage of time, as shown in FIG. 1D. However, in the ore7 mutant of the present invention, there were little or no changes in the expression patterns of these genes. Meanwhile, it was found that, in the wild type, the expression of various senescence-associated genes, such as SAG12 and SEN4, was increased with the passage of time, but in the ore7 mutant, the expression patterns of the senescence-associated genes were not substantially increased in the same time. This fact suggests that the ore7 mutant delays the initiation of senescence at the physiological level and also at the molecular level, thereby extending the leaf longevity. In addition, the above results were coincident with the results of study indicating that anabolic activity such as photosynthesis and self-maintenance activity are increased with the growth of leaves and then decreased at the senescence stage (H. G. Nam, *Curr. Opin. Biotech,* 8:200, 1997).

EXAMPLE 4

Examination of a Change in Leaf Longevity of ore7 Mutant According to Dark Treatment A change in leaf longevity of the ore7 mutant under dark treatment known as accelerating senescence was examined by measuring changes in photosynthesis activity and chlorophyll content.

Figure 2A:
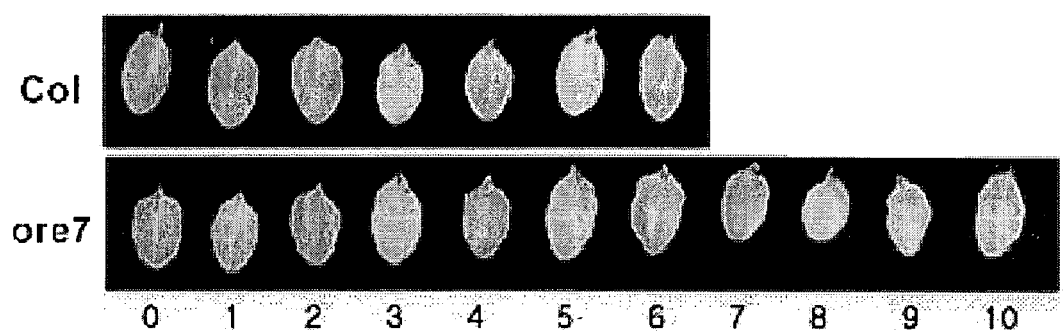
FIG. 2A is a photograph illustrating leaf senescence depending on time after dark treatment, in the wild type *Arabidopsis thaliana* (Col) and in the longevity-extended mutant ore7.
Figure 2B:
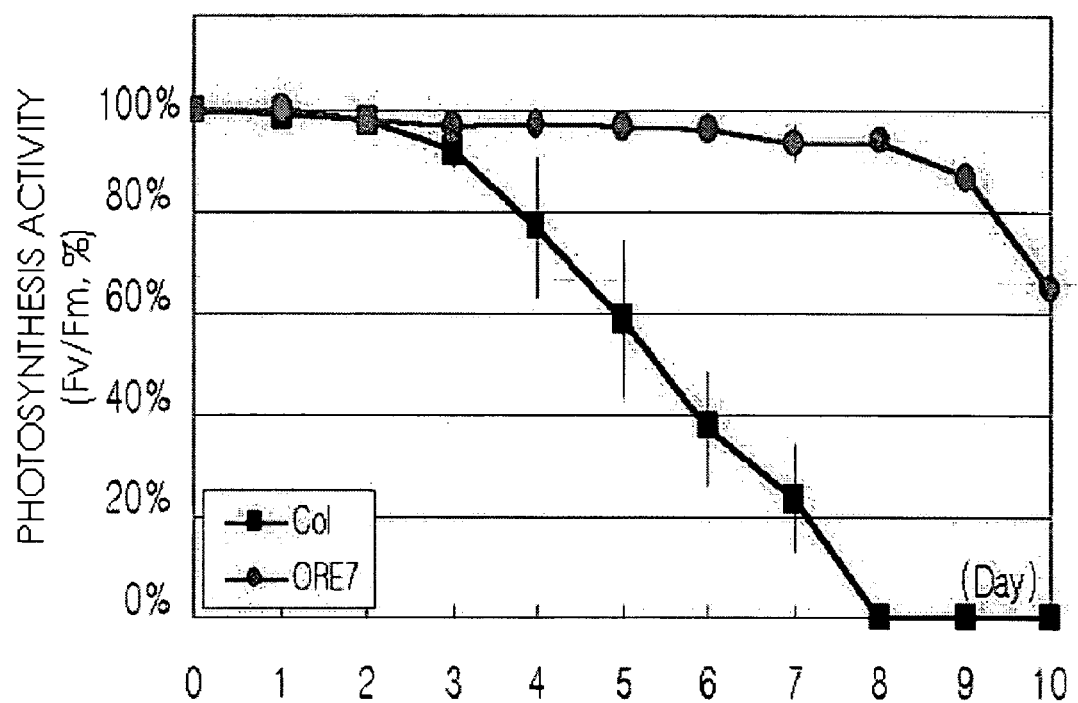
FIG. 2B is a graph showing a change in photosynthesis activity depending on time after dark treatment, in the wild type *Arabidopsis thaliana* (Col) and in the longevity-extended mutant ore7.
Figure 2C:
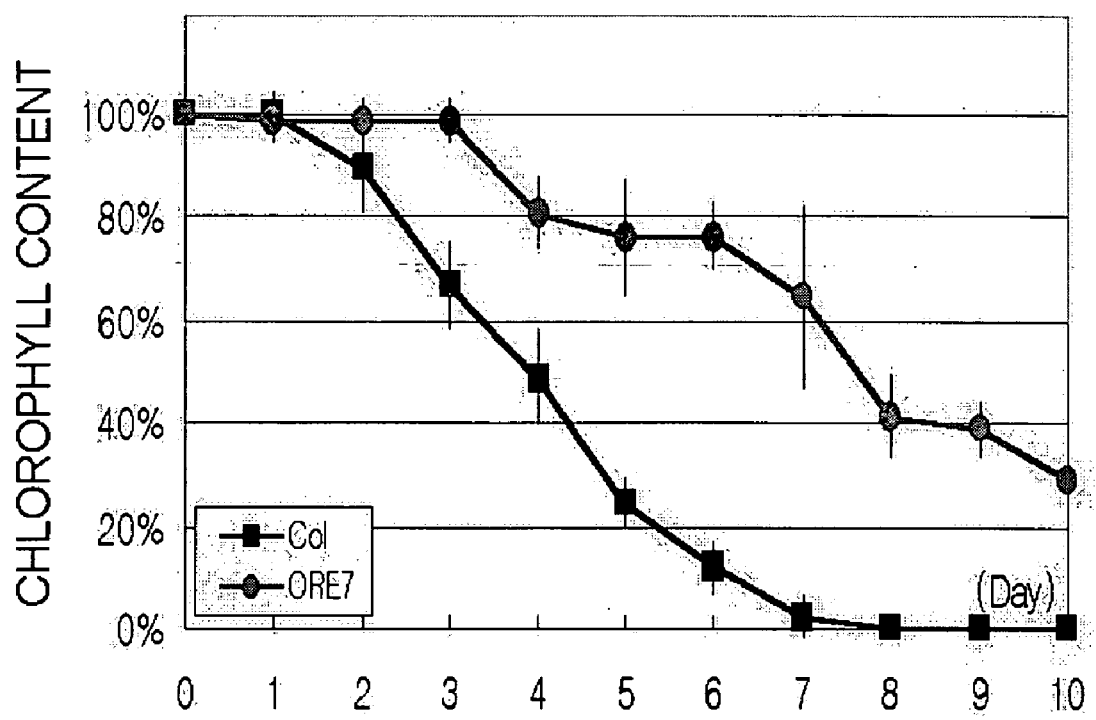
FIG. 2C is a graph showing a change in chlorophyll content depending on time after dark treatment, in the wild type *Arabidopsis thaliana* (Col) and in the longevity-extended mutant ore7.

12 independent leaves at 25 DAG were detached from the wild type *Arabidopsis thaliana* and the ore7 mutant, and floated in 2 ml of 3 mM 2-[N-morpholino]-ethanesulfonic acid buffer, pH 5.8 hereinafter, referred to as "MES buffer"). The resulting leaves were measured for photosynthesis activity and chlorophyll content, every day, in the same manner as in Example 2, while storing in a light impermeable box at 22° C. Results showed that the photosynthesis activity in the wild type was decreased to 60% at 5 days after the dark treatment, but the ore7 mutant maintained the photosynthesis activity of 97%, as shown in FIG. 2B. In addition, it was found that the reduction pattern of the chlorophyll content became blunt in the case of the ore7 mutant, similar to the photosynthesis activity, so that the ore7 mutant exhibited the chlorophyll content of 75% that is three times as large as that of the wild type whereas the wild type exhibited the chlorophyll content of 25%, at 5 days after the dark treatment, as shown in FIG. 2C.

Figure 2D:
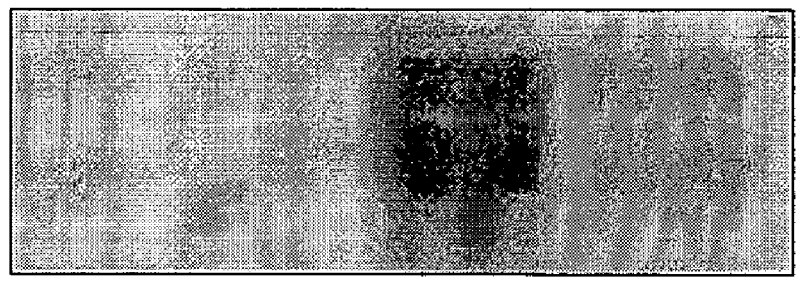
FIG. 2D shows the results of northern blot analysis illustrating the expression pattern of a senescence-associated gene (SEN4) in the wild type *Arabidopsis thaliana* (Col) and in the longevity-extended mutant ore7 after dark treatment.

Moreover, the expression of a SEN4 gene, a measure of senescence molecules, was examined in the same manner as described in Example 3. Results indicated that the expression of SEN4 in the wild type was highly increased, compared to the ore7 mutant, as shown in FIG. 2D.

EXAMPLE 5

Changes in Leaf Longevity of ore7 Mutant According to Treatment with Phytohormones Further, in the present invention, a change in leaf longevity of the ore7 mutant according to treatment with phytohormones, such as ABA, MeJA and ethylene that are involved in senescence regulation was examined by measuring changes in photosynthesis activity and chlorophyll content. 12 independent leaves at 25 DAG were floated in 2 ml of MES buffer containing 50 µM ABA or 50 µM MeJA. Treatment with ethylene was carried out by culturing *Arabidopsis thaliana* in a glass box containing 4.5 µM ethylene gas. As a negative control group, MES buffer not containing ABA or MeJA was used. The treatments with phytohormones as described above were carried out for three days at 22° C. with continuous exposure to light. The chlorophyll content and the photosynthesis activity were measured in the same manner as described in Example 2.

Results showed that, in the case of the negative control group (treated with only MES buffer not containing ABA or MeJA), as shown in FIGS. 3A and 4A, there are no changes in photosynthesis activities and chlorophyll contents of the wild type and the ore7 mutant. On the other hand, as shown in FIGS. 3B to 3D, the photosynthesis activity in the wild type was rapidly decreased from 2 days after treatment with ABA, MeJA and ethylene, respectively, but the ore7 mutant exhibited a slight decrease in the photosynthesis activity. Furthermore, as shown in FIGS. 4B to 4D, a reduction in the chlorophyll content became blunt in the case of the ore7 mutant, similar to the photosynthesis activity. These results suggest that the ore7 mutant has low susceptibility to the senescence-accelerating hormones.

EXAMPLE 6

Cloning and Sequencing of ORE7 Gene

In order to investigate a gene around T-DNA activated by an enhancer, the genes was isolated from the ore7 mutant according to the plasmid rescue method (Weigel et al., *Plant Physiology*, 122:1003–1014, 2000). FIG. 6 is a scheme showing that an activation tagging vector pSKI015 is inserted into a genome of the longevity-extended mutant ore7. First, the total genomic DNA of the ore7 mutant was isolated by the method described by Dellaporta et al. (Dellaporta et al., *Plant Mol. Biol. Rep.*, 1:19–21, 1983). After this, 5 μg of genomic DNA was digested with EcoRI restriction enzyme, purified by ethanol precipitation, and then dried. The digested DNA was self-ligated, and transformed into DH5α. An ampicillin-resistant colony was selected out of transformants. A plasmid was isolated from the selected colony, and a nucleotide sequence of a region which is 4.0 kb apart from the right border of T-DNA was determined using an oligomer constructed based on a nucleotide sequence downstream of the EcoRI region which had been used in the above plasmid rescue method. The determined nucleotide sequence was searched with reference to the *Arabidopsis thaliana* genome database, thereby investigating a open reading frame closest to an enhancer. The identified open reading frame was termed 'ORE7 gene' whose nucleotide sequence is represented by SEQ ID NO: 1. It could be found that protein expressed from the ORE7 gene consists of 311 amino acids, as shown in SEQ ID NO: 2. Further, it could be found that an AT-hook motif is present at 83–94 region of the amino acid sequence represented by SEQ ID NO: 2, and glycine-, histidine-, glutamine-, and glutamic acid-rich motifs are present at 38–52 and 245–261 regions of the amino acid sequence.

Thereafter, northern blot analysis was carried out using the ORE7 gene as a probe. Total RNAs were extracted from the wild type and the ore7 mutant, respectively, using Tri-reagent (Sigma), according to the method by Woo et al. (Woo H. R. et al. *Plant Cell*, 13:1779–1790, 2001). 10 μg of RNA was loaded onto a 1.2% agarose/formaldehyde gel, every lane, isolated, then blotted to a nylon membrane. The resulting RNA sample was washed with 3×SSC for 5 minutes to remove an excess of agarose. Then, in order to immobilize the RNA sample to the nylon membrane, irradiation with ultraviolet ray (254 nm, 0.18 J/cm$^2$) was carried out. The resulting blot was subjected to prehybridization and hybridization according to the method by Park et al. (Park et al., *Plant Mol. Biol*, 26:1725–1735, 1994).

Results showed that there is little or no expression of the ORE7 gene in the wild type, whereas in the ore7 mutant, the ORE7 gene is expressed at significantly high transcription concentration, as shown in FIG. 7.

EXAMPLE 7

Introduction of ORE7 Gene into Wild Type *Arabidopsis thaliana*

In order to finally determine whether the senescence-delaying phenotype occurring in the ore7 mutant is caused by activation of the OER7 gene, experiments in which a DNA fragment of 5.4 kb size containing an enhancer and the ORE7 gene is introduced into the wild type *Arabidopsis thaliana* were carried out.

For this, the plasmid obtained by the plasmid rescue method was digested with BamHI and EcoRI, thereby isolating a DNA fragment containing the ORE7 gene and an enhancer. The digested DNA fragment was inserted into a pCAMBIA3301 vector (MRC, USA) digested with BamHI and EcoRI. The resulting vector was termed 'pORE7/3301'. An *Agrobacterium tumefacience* AGL1 strain (Lazo G. R., et al., *Biotechnology*, 9:963–967, 1991) (ATCC BAA-101) was then transformed with the recombinant vector pORE7/3301. The transformed *Agrobacterium tumefacience* strain was termed 'pAT-ORE7' and deposited under the accession number KCTC 10032BP on Aug. 8, 2001 with the Korean Collection for Type Cultures (KCTC). Then, the wild type *Arabidopsis thaliana* (Columbia) was transformed with pAT-ORE7 by the floral tip method (Clough et al., *Plant J.*, 16(6): 735–743, 1998). The transformed *Arabidopsis thaliana* was bred, thereby obtaining seeds, and herbicide-resistant transformants were selected from the seeds. The transformed *Arabidopsis thaliana* was grown in a greenhouse, and examined for senescence-delaying patterns. Results showed that the senescence-delaying phenotype that was exhibited in the ore7 mutant is reproduced as it is. This suggests that the senescence-delaying phenotype is exhibited by activation of the ORE7 gene, and activation of the ORE7 gene in plants can induce senescence delay in the plants.

EXAMPLE 8

Examination on Expression of GFP-ORE7 Fusion Protein in Epidermal Cells of Onions A polypeptide sequence deduced from the nucleotide sequence of ORE7 gene determined in Example 6 was searched with databases. Results showed that it has an AT-hook motif and also glycine-, histidine-, glutamine-, and glutamic acid-rich motifs. These motifs are those found in the transcription factor or transcription regulator of regulating the expression of other genes in nuclei. Therefore, the present inventors have determined whether the ORE7 protein of the present invention migrates into the nuclei or not.

First, a gene encoding the total ORE7 protein was amplified by PCR with primers represented by SEQ ID NO: 3 and SEQ ID NO: 4. The PCR reaction was initiated by heating to 95° C. for 2 minutes, then subjected to 35 cycles under the condition as the following: 94° C. for 30 seconds, 55° C. for 30 seconds, and 72° C. for 1 minute, and completed by finally amplifying for 10 minute at 72° C. A DNA fragment of a 0.95 kb size obtained by the above PCR was isolated by agarose gel electrophoresis, and then was inserted into SmaI and HindIII restriction enzyme sites of a 326 GFP-3G plasmid (obtained from Professor In-Hwan, Hwang, Pohang University of Science and Technology Foundation, Korea) containing a gene of a green fluorescence protein (GFP), thereby constructing a plasmid pGFP-ORE7. Following this, the expression of a GFP-ORE7 fusion protein in epidermal cells of onions was examined according to the method by Varagona et al (Varagona et al., *Plant Cell*, 4:1213–1227, 1992). For coating of tungsten particles with DNA, a plasmid expressing the ORE7-GFP fusion protein was purified using a Qiagen column, and then 2 μg of DNA was precipitated with tungsten particles in a solution containing 50 μl of 2.5 M CaCl$_2$ and 20 μl of 0.1 M spermidine. The precipitates were washed with 70% ethanol, and then resuspended in 36 μl of 100% ethanol. Subsequently, epidermal cells of onions were placed on a ½ B5 medium in a petri dish in such a manner that the inner coat of the onion faced upward. Then, the M-25 tungsten particle coated with the plasmid DNA was subjected to particle bombardment using 1350 p.s.i.

(Biorad). The petri dish was wrapped with parafilm, and then incubated in an incubator at 22° C. for 18 hours. After 18 hours, the expression of GFP was observed with a fluorescence microscope.

Results showed that the expression of ORE7-GFP occurs within the nuclei, as shown in FIG. 8. This suggests that the ORE7 protein migrates into the nuclei and functions therein.

INDUSTRIAL APPLICABILITY

As apparent from the foregoing, it was found that the senescence-delaying phenotype of the ore7 mutant occurs by activation of the ORE7 gene, and activation of the ORE7 gene can induce the delay of senescence in plants. Plants can be transformed with the ORE7 gene regulating the leaf longevity of plants according to the present invention, so that the longevity of the plants is increased, thereby improving productivity and storage efficiency of the plants. Furthermore, the ORE7 gene and the ORE7 protein expressed therefrom according to the present invention are useful for studies of senescence mechanisms, and for investigation of senescence-associated genes or senescence inhibitory substances, in plants.

What is claimed is:

1. An *Agrobacterium tumefacience* pAT-ORE7 (accession number: KCTC 10032BP) transformed with a recombinant vector comprising a polynucleotide comprising a sequence encoding an amino acid sequence represented by SEQ ID NO: 2.

2. A method for increasing the longevity of leaves of a plant, comprising introducing a polynucleotide comprising a sequence encoding an amino acid sequence represented by SEQ ID NO: 2 into said plant so that it is overexpressed, and selecting for transformed plants wherein the longevity of leaves is increased compared to non-transformed plants of the same species.

3. The method according to claim 2, wherein the polynucleotide comprises the nucleotide sequence represented by SEQ ID NO: 1.

4. The method according to claim 2, wherein the plants are selected from among food crops, fruit trees, flower crops, and fodder crops.

5. The method according to claim 4, wherein the plants are food crops selected from among rice plant, wheat, barley, corn, bean, potato, Indian bean, oat and Indian millet; vegetable crops comprising *Arabidopsis* sp., Chinese cabbage, radish, red pepper, strawberry, tomato, watermelon, cucumber, cabbage, melon, pumpkin, welsh onion, onion and carrot.

6. The method according to claim 4, wherein the plants are fruit trees selected from among apple tree, pear tree, jujube tree, peach tree, kiwi fruit tree, grape tree, citrus fruit tree, persimmon tree, plum tree, apricot tree and banana tree.

7. The method according to claim 4, wherein the plants are flower crops selected from among rose, gladiolus, gerbera, carnation, chrysanthemum, lily and tulip.

8. The method according to claim 4, wherein the plants are fodder crops selected from among ryegrass, red clover, orchardgrass, alfalfa, tallfescue and perennial ryegrass.

9. The method according to claim 2, wherein the plants are selected from among ginseng, tobacco plant, cotton plant, sesame, sugar cane, sugar beet, *Perilla* sp., peanut and rape.

* * * * *

SEQUENCE LISTING

<160> NUMBER OF SEQ ID NOS: 4

<210> SEQ ID NO 1
<211> LENGTH: 936
<212> TYPE: DNA
<213> ORGANISM: Arabidopsis thaliana

<400> SEQUENCE: 1

```
atggaaggcg gttacgagca aggcggtgga gcttctagat acttccataa cctctttaga      60
ccggagattc accaccaaca gcttcaaccg cagggcggga tcaatcttat cgaccagcat     120
catcatcagc accagcaaca tcaacaacaa caacaaccgt cggatgattc aagagaatct     180
gaccattcaa acaaagatca tcatcaacag ggtcgacccg attcagaccc gaatacatca     240
agctcagcac cgggaaaacg tccacgtgga cgtccaccag gatctaagaa caaagccaag     300
ccaccgatca tagtaactcg tgatagcccc aacgcgctta gatctcacgt tcttgaagta     360
tctcctggag ctgacatagt tgagagtgtt tccacgtacg ctaggaggag agggagaggc     420
gtctccgttt taggaggaaa cggcaccgta tctaacgtca ctctccgtca gccagtcact     480
cctggaaatg gcggtggtgt gtccggagga ggaggagttg tgactttaca tggaaggttt     540
gagattcttt cgctaacggg gactgttttg ccacctcctg caccgcctgg tgccggtggt     600
ttgtctatat ttttagccgg agggcaaggt caggtggtcg gaggaagcgt tgtggctccc     660
cttattgcat cagctccggt tatactaatg gcggcttcgt tctcaaatgc ggttttcgag     720
agactaccga ttgaggagga ggaagaagaa ggtggtggtg gcggaggagg aggaggagga     780
gggccaccgc agatgcaaca agctccatca gcatctccgc cgtctggagt gaccggtcag     840
ggacagttag gaggtaatgt gggtggttat gggttttctg gtgatcctca tttgcttgga     900
tgggagctg gaacaccttc aagaccacct tttaa                                 936
```

<210> SEQ ID NO 2
<211> LENGTH: 311
<212> TYPE: PRT
<213> ORGANISM: Arabidopsis thaliana

<400> SEQUENCE: 2

```
Met Glu Gly Gly Tyr Glu Gln Gly Gly Gly Ala Ser Arg Tyr Phe His
 1               5                  10                  15

Asn Leu Phe Arg Pro Glu Ile His His Gln Gln Leu Gln Pro Gln Gly
             20                  25                  30

Gly Ile Asn Leu Ile Asp Gln His His Gln His Gln Gln His Gln
         35                  40                  45

Gln Gln Gln Gln Pro Ser Asp Asp Ser Arg Glu Ser Asp His Ser Asn
     50                  55                  60
```

Lys Asp His His Gln Gln Gly Arg Pro Asp Ser Asp Pro Asn Thr Ser
65                  70                  75                  80

Ser Ser Ala Pro Gly Lys Arg Pro Arg Gly Arg Pro Pro Gly Ser Lys
            85                  90                  95

Asn Lys Ala Lys Pro Pro Ile Ile Val Thr Arg Asp Ser Pro Asn Ala
        100                 105                 110

Leu Arg Ser His Val Leu Glu Val Ser Pro Gly Ala Asp Ile Val Glu
    115                 120                 125

Ser Val Ser Thr Tyr Ala Arg Arg Gly Arg Gly Val Ser Val Leu
130                 135                 140

Gly Gly Asn Gly Thr Val Ser Asn Val Thr Leu Arg Gln Pro Val Thr
145                 150                 155                 160

Pro Gly Asn Gly Gly Val Ser Gly Gly Gly Val Val Thr Leu
                165                 170                 175

His Gly Arg Phe Glu Ile Leu Ser Leu Thr Gly Thr Val Leu Pro Pro
            180                 185                 190

Pro Ala Pro Pro Gly Ala Gly Gly Leu Ser Ile Phe Leu Ala Gly Gly
        195                 200                 205

Gln Gly Gln Val Val Gly Gly Ser Val Val Ala Pro Leu Ile Ala Ser
210                 215                 220

Ala Pro Val Ile Leu Met Ala Ala Ser Phe Ser Asn Ala Val Phe Glu
225                 230                 235                 240

Arg Leu Pro Ile Glu Glu Glu Glu Glu Gly Gly Gly Gly Gly
                245                 250                 255

Gly Gly Gly Gly Gly Pro Pro Gln Met Gln Gln Ala Pro Ser Ala Ser
            260                 265                 270

Pro Pro Ser Gly Val Thr Gly Gln Gly Gln Leu Gly Gly Asn Val Gly
        275                 280                 285

Gly Tyr Gly Phe Ser Gly Asp Pro His Leu Leu Gly Trp Gly Ala Gly
290                 295                 300

Thr Pro Ser Arg Pro Pro Phe
305                 310

<210> SEQ ID NO 3
<211> LENGTH: 31
<212> TYPE: DNA
<213> ORGANISM: Artificial Sequence
<220> FEATURE:
<223> OTHER INFORMATION: 5' primer for PCR of ORE7 gene

<400> SEQUENCE: 3
tacccgggca atggaaggcg gttacgagca a        31

<210> SEQ ID NO 4
<211> LENGTH: 33
<212> TYPE: DNA
<213> ORGANISM: Artificial Sequence
<220> FEATURE:
<223> OTHER INFORMATION: 3' primer for PCR of ORE7 gene

<400> SEQUENCE: 4
cccaagcttt taaaaggtg gtcttgaagg tgt        33